US005869309A

United States Patent [19]
Politino et al.

[11] Patent Number: 5,869,309
[45] Date of Patent: Feb. 9, 1999

[54] **CEPHALOSPORIN ESTERASE GENE FROM *RHODOSPORIDIUM TORULOIDES***

[75] Inventors: Michael Politino, Syracuse; Sean M. Tonzi, Skaneateles; John J. Usher, East Syracuse; William V. Burnett, Fayetteville; Guna Romancik, Jamesville, all of N.Y.

[73] Assignee: Bristol-Myers Squibb Co., New York, N.Y.

[21] Appl. No.: 932,376

[22] Filed: Sep. 17, 1997

Related U.S. Application Data

[60] Provisional application No. 60/026,929 Sep. 18, 1996.
[51] Int. Cl.$^6$ .............................. C12N 9/18; C12N 15/00; C12N 15/63; C07H 21/04
[52] U.S. Cl. ...................... 435/197; 435/69.1; 435/320.1; 435/325; 435/252.33; 435/254.11; 435/254.5; 536/23.1; 536/23.2; 536/23.74
[58] Field of Search ................................ 435/197, 320.1, 435/252.1, 325, 69.1; 536/23.1

[56] References Cited

U.S. PATENT DOCUMENTS

| | | |
|---|---|---|
| 4,533,632 | 8/1985 | Smith et al. ............................ 435/47 |
| 5,512,454 | 4/1996 | Usher et al. ............................ 435/47 |

OTHER PUBLICATIONS

Abbott, B.J., and D. Fukuda. 1975. Appl. Microbiol 30:413–419.
Bradford, M.M. 1976. Anal. Biochem. 72:248–254.
Davis, B. 1964. N.Y. Acad. Sci. 121 part II:404–427.
Demain, A.L., R.B. Walton, J.F. Newkirk and I.M. Miller. 1963. Nature (London) 199:909–910.
Elder, J.H. and S. Alexander. 1982. Proc. Natl. Acad. Sci. USA 79:4540–4544.
Fujisawa, Y., H. Shirafuji and T. Kanzaki. 1975. Agric. Biol. Chem. 39:1303–1309.
Harper, J.W., K. Hemmi and J.C. Powers. 1985. Biochemistry 24:1831–1841.
Huber, F.M., R.H. Baltz and P.G. Caltrider. 1968. Appl. Microbiol. 16:1011–1014.
Jeffery, J. D'A., E.P. Abraham and G.G.F. Newton. 1961. Biochem. J. 81:591–596.
Kirsch, K. 1971. In P.D. Boyer (ed.), The enzymes, vol. 5, Academic Press, London and New York, pp. 43–69.
Konecny, J. and W. Voser. 1977. Biochim. Biophys. Acta. 485:367–378.
Laemmli, U.K. 1970. Nature (London) 227:680–685.
O'Callaghan, C.H. and P.W. Muggleton. 1963. Biochem. J. 89:304–308.
Takimoto, A., K. Mitsushima, S. Yagi and T. Sonoyama. 1994. J. Ferment. Biong. 77:17–22.
Trimble, R.B. and F. Maley. 1984. Anal. Biochem. 141:515–522.

*Primary Examiner*—Rebecca E. Prouty
*Assistant Examiner*—Peter P. Tung
*Attorney, Agent, or Firm*—Thomas R. Savitsky; Christopher A. Klein; Audrey F. Sher

[57] ABSTRACT

The instant invention provides nucleic acid molecules encoding cephalosporin esterase from Rhodosporidium toruloides. In addition, the invention provides isolated cephalosporin esterase, expression vectors, host cells, and methods of producing cephalosporin esterase.

24 Claims, 10 Drawing Sheets

| | | | | | | |
|---|---|---|---|---|---|---|
| AMINO ACID SEQ. | T | N | P | N | E | P |
| REV. TRANSLATION | ACX | AAPy | CCX | AAPy | GAPu | CC |
| INVERSE | GGPy | TCPu | TTX | GGPu | TTX | GT |
| PROBE 1 | GGPy | TCPu | TTG | GGPu | TTX | GT |
| 2 | | | A | | | |
| 3 | | | T | | | |
| 4 | | | C | | | |

Four 17-mer oligonucleotide probes each with a 32-fold degeneracy were synthesized from the N-terminal amino acid sequence and used to probe a Southern blot of *R.toruloides* DNA

FIG. 4

```
ACTCGCCGCCATGCTCCTTAACCTCTTCACCCTCGCCTCCCTCGCTGCGACGCTCCAGCT        60
  L  A  A  M  L  L  N  L  F  T  L  A  S  L  A  A  T  L  Q  L

CGCCTTTGCCTCTCCGACCTCCCTCGTCCGCCGCACGAACCCAAACGAGCCCCCTCCCGT       120
  A  F  A  S  P  T  S  L  V  R  R  T  N  P  N  E  P  P  P  V

CGTCGACCTCGGCTACGCCCGCTACCAAGGCTACTTGAACGAGACCGCCGGACTCTACTG       180
  V  D  L  G  Y  A  R  Y  Q  G  Y  L  N  E  T  A  G  L  Y  W

GTGGCGCGGAATCCGCTACGCCTCGGCTCAGCGCTTCCAGGCTCCTCAGACGCCCGCGAC       240
  W  R  G  I  R  Y  A  S  A  Q  R  F  Q  A  P  Q  T  P  A  T

GCACAAGGCCGTCCGCAACGCGACTGAGTATGGACCGATCTGTTGGCCGGCTAGCGAGGG       300
  H  K  A  V  R  N  A  T  E  Y  G  P  I  C  W  P  A  S  E  G

AACCAACACGACCAAGGGCTTGCCGCCGCCTAGCAACAGCTCGAGCAGCGCGCCGCAGAA       360
  T  N  T  T  K  G  L  P  P  P  S  N  S  S  S  A  P  Q  K

ACAGGCGTCGGAGGATTGCCTCTTCCTCAATGTCGTTGCCCCCGCCGGCTCGTGCGAGGG       420
  Q  A  S  E  D  C  L  F  L  N  V  V  A  P  A  G  S  C  E  G

CGACAATCTTCCCGTCCTCGTCTACATTCACGGAGGTGGCTACGCCTTCGGCGATGCGAG       480
  D  N  L  P  V  L  V  Y  I  H  G  G  G  Y  A  F  G  D  A  S

CACCGGCAGCGACTTTGCCGCCTTCACCAAGCACACGGGAACCAAGATGGTCGTTGTAAA       540
  T  G  S  D  F  A  A  F  T  K  H  T  G  T  K  M  V  V  V  N

TCTCCAGTACCGTCTCGGCAGCTTTGGTTTCCTCGCTGGCCAAGCCATGAAGGACTACGG       600
  L  Q  Y  R  L  G  S  F  G  F  L  A  G  Q  A  M  K  D  Y  G

TGTAACGAACGCCGGCTTGCTTGACCAGCAATTCGCCCTTCAATGGGTTCAACAGCACGT       660
  V  T  N  A  G  L  L  D  Q  Q  F  A  L  Q  W  V  Q  Q  H  V

CTCGAAGTTCGGCGGCAACCCCGATCACGTTACGATTTGGGGCGAGTCTGCAGGCGCAGG       720
  S  K  F  G  G  N  P  D  H  V  T  I  W  G  E  S  A  G  A  G

GTCCGTTATGAACCAGATCATTGCGAACGGCGGCAACACCGTCAAGGCTCTCGGTCTCAA       780
  S  V  M  N  Q  I  I  A  N  G  G  N  T  V  K  A  L  G  L  K

GAAGCCCCTCTTCCACGCTGCCATCGGCTCCTCCGTCTTCCTCCCCTACCAAGCCAAGTA       840
  K  P  L  F  H  A  A  I  G  S  S  V  F  L  P  Y  Q  A  K  Y

CAACTCCCCCTTCGCCGAGCTGCTCTACTCCCAACTCGTCTCGGCGACAAACTGCACCAA       900
  N  S  P  F  A  E  L  L  Y  S  Q  L  V  S  A  T  N  C  T  K

AGCCGCCTCGTCCTTCGCTTGCCTCGAAGCTGTCGACGCTGCGGCGCTCGCTGCGGCGGG       960
  A  A  S  S  F  A  C  L  E  A  V  D  A  A  A  L  A  A  A  G

CGTGAAGAACTCGGCGGCGTTCCCGTTCGGGTTTTGGTCGTATGTCCCGGTCGTCGACGG      1020
  V  K  N  S  A  A  F  P  F  G  F  W  S  Y  V  P  V  V  D  G

GACCTTCTTGACTGAGCGCGCGTCGCTCCTTCTCGCCAAGGGCAAGAAGAACCTCAATGG      1080
  T  F  L  T  E  R  A  S  L  L  L  A  K  G  K  K  N  L  N  G

CAACCTCTTCACCGGGATCAACAACCTCGACGAAGGATTCATATTCACTGACGCCACTAT      1140
```

FIG. 5A

```
                N  L  F  T  G  I  N  N  L  D  E  G  F  I  F  T  D  A  T  I
TCAGAACGACACGATCAGCGACCAGTCGCAGCGCGTCTCCCAGTTCGACCGCCTCCTCGC    1200
 Q  N  D  T  I  S  D  Q  S  Q  R  V  S  Q  F  D  R  L  L  A
CGGCCTCTTCCCCTACATCACCTCGGAGGAGCGCCAGGCCGTCGCGAAGCAGTACCCGAT    1260
 G  L  F  P  Y  I  T  S  E  E  R  Q  A  V  A  K  Q  Y  P  I
CTCCGACGCGCCGTCAAAGGGCAACACCTTCTCTCGCATCTCGGCCGTCATCGCGGACTC    1320
 S  D  A  P  S  K  G  N  T  F  S  R  I  S  A  V  I  A  D  S
GACCTTCGTCTGCCCGACCTACTGGACCGCCGAGGCGTTCGGCTCGTCCGCCCACAAGGG    1380
 T  F  V  C  P  T  Y  W  T  A  E  A  F  G  S  S  A  H  K  G
CCTCTTCGACTACGCGCCGGCTCACCACGCGACCGACAACTCGTACTACATCGGCTCCAT    1440
 L  F  D  Y  A  P  A  H  H  A  T  D  N  S  Y  Y  I  G  S  I
CTGGAACGGCAAGAAGTCGGTCTCGTCCGTCCAGTCCTTCGACGGCGCGCTCGGCGGCTT    1500
 W  N  G  K  K  S  V  S  S  V  Q  S  F  D  G  A  L  G  G  F
CATCGAGACGTTCAACCCGAACAACAACGCTGCCAACAAGACCATCAACCCTTACTGGCC    1560
 I  E  T  F  N  P  N  N  N  A  A  N  K  T  I  N  P  Y  W  P
GACGTTCGACTCGGGCAAGCAGCTCCTCTTCAACACGACGACGAGGGACACCCTCTCTCC    1620
 T  F  D  S  G  K  Q  L  L  F  N  T  T  T  R  D  T  L  S  P
CGCCGACCCGCGCATCGTTGAGACTTCAAGCTTGACCGACTTTGGCACGAGCCAGAAGAC    1680
 A  D  P  R  I  V  E  T  S  S  L  T  D  F  G  T  S  Q  K  T
CAAGTGCGACTTCTGGCGTGGGTCAATCTCGGTGAACGCGGGTCTCTAGGCGTCTTTC     1738
 K  C  D  F  W  R  G  S  I  S  V  N  A  G  L  *  A  S  F
```

FIG. 5B

```
GGATCCACCCGAACTCTGTCCCGCTTTCTGGCTTTCTTCCTTGCTGTCGCCCCATCGCCT         60

|-- Translation Start -->
TTCCCGACTCGCCGCCATGCTCCTTAACCTCTTCACCCTCGCCTCCCTCGCTGCGACGCT        120
                  M   L   L   N   L   F   T   L   A   S   L   A   A   T   L

|- Mature peptide ->
CCAGCTCGCCTTTGCCTCTCCGACCTCCCTCGTCCGCCGCACGAACCCAAACGAGCCCC         180
 Q   L   A   F   A   S   P   T   S   L   V   R   R   T   N   P   N   E   P   P TCCCGTCGTCGACCTCGGCTACGCCCGCTACCAAGGCTACTTGAACGAGACCGCCGGACT        240
 P   V   V   D   L   G   Y   A   R   Y   Q   G   Y   L   N   E   T   A   G   L CTACTGGTGGCGCGGAATCCGCTACGCCTCGGCTCAGCGCTTCCAGGCTCCTCAGACGCC        300
 Y   W   W   R   G   I   R   Y   A   S   A   Q   R   F   Q   A   P   Q   T   P CGCGACGCACAAGGCCGTCCGCAACGCGACTGAGTATGGACCGATCTGTTGGCCGGCTAG        360
 A   T   H   K   A   V   R   N   A   T   E   Y   G   P   I   C   W   P   A   S CGAGGGAACCAACACGACCAAGGGCTTGCCGCCGCCTAGCAACAGCTCGAGCAGCGCGCC        420
 E   G   T   N   T   T   K   G   L   P   P   P   S   N   S   S   S   A   P GCAGAAACAGGCGTCGGAGGATTGCCTCTTCCTCAATGTCGTTGCCCCCGCCGGCTCGTG        480
 Q   K   Q   A   S   E   D   C   L   F   L   N   V   V   A   P   A   G   S   C CGAGGGCGACAATCTTCCCGTCCTCGTCTACATTCACGGAGGTGGCTACGCCTTCGGCGA        540
 E   G   D   N   L   P   V   L   V   Y   I   H   G   G   G   Y   A   F   G   D TGCCAGCACCGGCAGCGACTTTGCCGCCTTCACCAAGCACACGGGAACCAAGATGGTCGT        600
 A   S   T   G   S   D   F   A   A   F   T   K   H   T   G   T   K   M   V   V TGTAAATCTCCAGTACCGTCTCGGCAGCTTTGGTTTCCTCGCTGGCCAAGCCATGAAGGA        660
 V   N   L   Q   Y   R   L   G   S   F   G   F   L   A   G   Q   A   M   K   D

[---- Intron #1 ----------
CTACGGTGTAACGAACGCCGGCTTGCTTGACCAGGTGAGTTTCCCGCATGATACCCGCCC        720
 Y   G   V   T   N   A   G   L   L   D   Q -----------------------------------}
ACCTTTCGACTCATGCTGACGCCTCTCCCGCTCGCAGCAATTCGCCCTTCAATGGGTTCA        780
                                     Q   F   A   L   Q   W   V   Q ACAGCACGTCTCGAAGTTCGGCGGCAACCCCGATCACGTTACGATTTGGGGCGAGTCTGC        840
 Q   H   V   S   K   F   G   G   N   P   D   H   V   T   I   W   G   E   S   A

[---- Intron #2 -------
AGGCGCAGGGTCCGTTATGAACCAGATCATTGCGAACGTGAGCCACCCGAACCGATCTCC        900
 G   A   G   S   V   M   N   Q   I   I   A   N --------------------------------------------}
AGCCGACTTTCCCCCCCCCCCCCCCCCGCTGACCTCCCTCGTCTTGCAGGGCGGCAACA         960
                                                    G   G   N   T CCGTCAAGGCTCTCGGTCTCAAGAAGCCCCTCTTCCACGCTGCCATCGGCTCCTCCGTCT        1020
 V   K   A   L   G   L   K   K   P   L   F   H   A   A   I   G   S   S   V   F TCCTCCCCTACCAAGCCAAGTACAACTCCCCCTTCGCCGAGCTGCTCTACTCCCAACTCG        1080
 L   P   Y   Q   A   K   Y   N   S   P   F   A   E   L   L   Y   S   Q   L   V
```

FIG. 6A

```
TCTCGGCGACAAACTGCACCAAAGCCGCCTCGTCCTTCGCTTGCCTCGAAGCTGTCGACG         1140
  S   A   T   N   C   T   K   A   A   S   S   F   A   C   L   E   A   V   D   A

CTGCGGCGCTCGCTGCGGCGGGCGTGAAGAACTCGGCGGCGTTCCCGTTCGGGTTTTGGT         1200
  A   A   L   A   A   A   G   V   K   N   S   A   A   F   P   F   G   F   W   S

CGTATGTCCCGGTCGTCGACGGGACCTTCTTGACTGAGCGCGCGTCGCTCCTTCTCGCCA         1260
  Y   V   P   V   V   D   G   T   F   L   T   E   R   A   S   L   L   L   A   K

[---- Intron #3 ----------------------
AGGGCAAGAAGAACCTCAATGGCGTGCGTGGCGAGCTTTCGAGTGCTTCAGGATCTCGCT         1320
  G   K   K   N   L   N   G ----------------------]                                       [---
GACACTGTCGACCGGCTCGCAGAACCTCTTCACCGGGATCAACAACCTCGACGAAGATGA         1380
                                    N   L   F   T   G   I   N   N   L   D   E   G ---- Intron #4 -----------------------------------------------)
GTTCCCGTCGACGGCTCTGTTCGCCCAGCGAGACTGACTTGTTCTTTTGCGAAGATTACG         1440

ATTCATATTCACTGACGCCACTATTCAGAACGACACGATCAGCGACCAGTCGCAGCGCGT         1500
  F   I   F   T   D   A   T   I   Q   N   D   T   I   S   D   Q   S   Q   R   V

CTCCCAGTTCGACCGCCTCCTCGCCGGCCTCTTCCCCTACATCACCTCGGAGGAGCGCCA         1560
  S   Q   F   D   R   L   L   A   G   L   F   P   Y   I   T   S   E   E   R   Q

GGCCGTCGCGAAGCAGTACCCGATCTCCGACGCGCCGTCAAAGGGCAACACCTTCTCTCG         1620
  A   V   A   K   Q   Y   P   I   S   D   A   P   S   K   G   N   T   F   S   R

[---- Intron #5 ------------
CATCTCGGCCGTCATCGCGGACTCGACCTTCGTGTGCGTTCCCCGTCGTCTTCTCCGAGT         1680
  I   S   A   V   I   A   D   S   T   F   V ---------------------------)
ATTCCGCTGACTTCCCGCTTGCCCGCAGCTGCCCGACCTACTGGACCGCCGAGGCGTTCG         1740
                                        C   P   T   Y   W   T   A   E   A   F   G GCTCGTCCGCCCACAAGGGCCTCTTCGACTACGCGCCGGCTCACCACGCGACCGACAACT         1800
  S   S   A   H   K   G   L   F   D   Y   A   P   A   H   H   A   T   D   N   S CGTACTACATCGGCTCCATCTGGAACGGCAAGAAGTCGGTCTCGTCCGTCCAGTCCTTCG         1860
  Y   Y   I   G   S   I   W   N   G   K   K   S   V   S   S   V   Q   S   F   D ACGGCGCGCTCGGCGGCTTCATCGAGACGTTCAACCCGAACAACAACGCTGCCAACAAGA         1920
  G   A   L   G   G   F   I   E   T   F   N   P   N   N   N   A   A   N   K   T CCATCAACCCTTACTGGCCGACGTTCGACTCGGGCAAGCAGCTCCTCTTCAACACGACGA         1980
  I   N   P   Y   W   P   T   F   D   S   G   K   Q   L   L   F   N   T   T   T CGAGGGACACCCTCTCTCCCGCCGACCCGCGCATCGTTGAGACTTCAAGCTTGACCGACT         2040
  R   D   T   L   S   P   A   D   P   R   I   V   E   T   S   S   L   T   D   F TTGGCACGAGCCAGAAGACCAAGTGCGACTTCTGGCGTGGGTCAATCTCGGTGAACGCGG         2100
  G   T   S   Q   K   T   K   C   D   F   W   R   G   S   I   S   V   N   A   G GTCTCTAGGCGTCTTTCCTTCCGACTTCCTTCGTTCTTTCGTTGTTTATTCTTGCAGTTC         2160
  L   *

CGTTGTATCGGCCATTCGTGCGTGTAGCTCACTCGAGTATAGACGTTGGCAAGTGCGAAA         2220
```

FIG. 6B

```
  |--Translation Start-->      |-Mature peptide->
LAAMLLNLFTLASLAATLQLAFASPTSLVRRTNPNEPPPVVDLGYARYQGYLNETAGLYW

WRGIRYASAQRFQAPQTPATHKAVRNATEYGPICWPASEGTNTTKGLPPPSNSSSSAPQK

QASEDCLFLNVVAPAGSCEGDNLPVLVYIHGGGYAFGDASTGSDFAAFTKHTGTKMVVVN

LQYRLGSFGFLAGQAMKDYGVTNAGLLDQQFALQWVQQHVSKFGGNPDHVTIWGESAGAG

SVMNQIIANGGNTVKALGLKKPLFHAAIGSSVFLPYQAKYNSPFAELLYSQLVSATNCTK

AASSFACLEAVDAAALAAAGVKNSAAFPFGFWSYVPVVDGTFLTERASLLLAKGKKNLNG

NLFTGINNLDEGFIFTDATIQNDTISDQSQRVSQFDRLLAGLFPYITSEERQAVAKQYPI

SDAPSKGNTFSRISAVIADSTFVCPTYWTAEAFGSSAHKGLFDYAPAHHATDNSYYIGSI

WNGKKSVSSVQSFDGALGGFIETFNPNNNAANKTINPYWPTFDSGKQLLFNTTTRDTLSP
                                         |->Stop site
ADPRIVETSSLTDFGTSQKTKCDFWRGSISVNAGLOASF
```

FIG. 7

Amino acid composition from 1 to 572
TRN 2-1738 RHODOSPORIDIUM ESTERASE cDNA

|   | Total | Percent |
|---|---|---|
| A | 67 | 11.7 |
| C | 7 | 1.2 |
| D | 25 | 4.4 |
| E | 16 | 2.8 |
| F | 35 | 6.1 |
| G | 49 | 8.6 |
| H | 9 | 1.6 |
| I | 21 | 3.7 |
| K | 25 | 4.4 |
| L | 48 | 8.4 |
| M | 4 | 0.7 |
| N | 35 | 6.1 |
| P | 31 | 5.4 |
| Q | 26 | 4.5 |
| R | 16 | 2.8 |
| S | 52 | 9.1 |
| T | 43 | 7.5 |
| V | 32 | 5.6 |
| W | 10 | 1.7 |
| Y | 21 | 3.7 |
| Acidic | 41 | 7.2 |
| Basic | 41 | 7.2 |
| Charged | 82 | 14.3 |
| Net Charge | 0 | 0.0 |
| Hydrophobic | 136 | 23.8 |
| Residues | 572 | |
| MW | 61334 | |

FIG. 8

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 1738 base pairs
        ( B ) TYPE: nucleic acid (C) STRANDEDNESS: both
(D) TOPOLOGY: linear (ii) MOLECULE TYPE: cDNA (ix) FEATURE:
 (A) NAME/KEY: CDS
 (B) LOCATION: 11..1726

(xi) SEQUENCE DESCRIPTION: SEQ ID NO:1:

```
ACTCGCCGCC ATG CTC CTT AAC CTC TTC ACC CTC GCC TCC CTC GCT GCG      49
           Met Leu Leu Asn Leu Phe Thr Leu Ala Ser Leu Ala Ala
            1               5                  10

ACG CTC CAG CTC GCC TTT GCC TCT CCG ACC TCC CTC GTC CGC CGC ACG      97
Thr Leu Gln Leu Ala Phe Ala Ser Pro Thr Ser Leu Val Arg Arg Thr
     15              20              25

AAC CCA AAC GAG CCC CCT CCC GTC GTC GAC CTC GGC TAC GCC CGC TAC     145
Asn Pro Asn Glu Pro Pro Pro Val Val Asp Leu Gly Tyr Ala Arg Tyr
 30              35              40                          45

CAA GGC TAC TTG AAC GAG ACC GCC GGA CTC TAC TGG TGG CGC GGA ATC     193
Gln Gly Tyr Leu Asn Glu Thr Ala Gly Leu Tyr Trp Trp Arg Gly Ile
                 50              55                      60

CGC TAC GCC TCG GCT CAG CGC TTC CAG GCT CCT CAG ACG CCC GCG ACG     241
Arg Tyr Ala Ser Ala Gln Arg Phe Gln Ala Pro Gln Thr Pro Ala Thr
             65              70              75

CAC AAG GCC GTC CGC AAC GCG ACT GAG TAT GGA CCG ATC TGT TGG CCG     289
His Lys Ala Val Arg Asn Ala Thr Glu Tyr Gly Pro Ile Cys Trp Pro
         80              85              90

GCT AGC GAG GGA ACC AAC ACG ACC AAG GGC TTG CCG CCG CCT AGC AAC     337
Ala Ser Glu Gly Thr Asn Thr Thr Lys Gly Leu Pro Pro Pro Ser Asn
     95              100             105

AGC TCG AGC AGC GCG CCG CAG AAA CAG GCG TCG GAG GAT TGC CTC TTC     385
Ser Ser Ser Ser Ala Pro Gln Lys Gln Ala Ser Glu Asp Cys Leu Phe
110             115             120                         125

CTC AAT GTC GTT GCC CCC GCC GGC TCG TGC GAG GGC GAC AAT CTT CCC     433
Leu Asn Val Val Ala Pro Ala Gly Ser Cys Glu Gly Asp Asn Leu Pro
                 130             135                     140

GTC CTC GTC TAC ATT CAC GGA GGT GGC TAC GCC TTC GGC GAT GCG AGC     481
Val Leu Val Tyr Ile His Gly Gly Gly Tyr Ala Phe Gly Asp Ala Ser
             145             150                     155

ACC GGC AGC GAC TTT GCC GCC TTC ACC AAG CAC ACG GGA ACC AAG ATG     529
Thr Gly Ser Asp Phe Ala Ala Phe Thr Lys His Thr Gly Thr Lys Met
         160             165                     170

GTC GTT GTA AAT CTC CAG TAC CGT CTC GGC AGC TTT GGT TTC CTC GCT     577
Val Val Val Asn Leu Gln Tyr Arg Leu Gly Ser Phe Gly Phe Leu Ala
     175             180             185

GGC CAA GCC ATG AAG GAC TAC GGT GTA ACG AAC GCC GGC TTG CTT GAC     625
Gly Gln Ala Met Lys Asp Tyr Gly Val Thr Asn Ala Gly Leu Leu Asp
190             195             200                         205

CAG CAA TTC GCC CTT CAA TGG GTT CAA CAG CAC GTC TCG AAG TTC GGC     673
Gln Gln Phe Ala Leu Gln Trp Val Gln Gln His Val Ser Lys Phe Gly
                 210             215                     220

GGC AAC CCC GAT CAC GTT ACG ATT TGG GGC GAG TCT GCA GGC GCA GGG     721
Gly Asn Pro Asp His Val Thr Ile Trp Gly Glu Ser Ala Gly Ala Gly
             225             230                     235

TCC GTT ATG AAC CAG ATC ATT GCG AAC GGC GGC AAC ACC GTC AAG GCT     769
Ser Val Met Asn Gln Ile Ile Ala Asn Gly Gly Asn Thr Val Lys Ala
         240             245                     250

CTC GGT CTC AAG AAG CCC CTC TTC CAC GCT GCC ATC GGC TCC TCC GTC     817
Leu Gly Leu Lys Lys Pro Leu Phe His Ala Ala Ile Gly Ser Ser Val
     255             260             265

TTC CTC CCC TAC CAA GCC AAG TAC AAC TCC CCC TTC GCC GAG CTG CTC     865
```

```
Phe Leu Pro Tyr Gln Ala Lys Tyr Asn Ser Pro Phe Ala Glu Leu Leu
270             275             280             285

TAC TCC CAA CTC GTC TCG GCG ACA AAC TGC ACC AAA GCC GCC TCG TCC      913
Tyr Ser Gln Leu Val Ser Ala Thr Asn Cys Thr Lys Ala Ala Ser Ser
            290             295             300

TTC GCT TGC CTC GAA GCT GTC GAC GCT GCG GCG CTC GCT GCG GCG GGC      961
Phe Ala Cys Leu Glu Ala Val Asp Ala Ala Ala Leu Ala Ala Ala Gly
            305             310             315

GTG AAG AAC TCG GCG GCG TTC CCG TTC GGG TTT TGG TCG TAT GTC CCG     1009
Val Lys Asn Ser Ala Ala Phe Pro Phe Gly Phe Trp Ser Tyr Val Pro
            320             325             330

GTC GTC GAC GGG ACC TTC TTG ACT GAG CGC GCG TCG CTC CTT CTC GCC     1057
Val Val Asp Gly Thr Phe Leu Thr Glu Arg Ala Ser Leu Leu Leu Ala
        335             340             345

AAG GGC AAG AAG AAC CTC AAT GGC AAC CTC TTC ACC GGG ATC AAC AAC     1105
Lys Gly Lys Lys Asn Leu Asn Gly Asn Leu Phe Thr Gly Ile Asn Asn
350             355             360             365

CTC GAC GAA GGA TTC ATA TTC ACT GAC GCC ACT ATT CAG AAC GAC ACG     1153
Leu Asp Glu Gly Phe Ile Phe Thr Asp Ala Thr Ile Gln Asn Asp Thr
            370             375             380

ATC AGC GAC CAG TCG CAG CGC GTC TCC CAG TTC GAC CGC CTC CTC GCC     1201
Ile Ser Asp Gln Ser Gln Arg Val Ser Gln Phe Asp Arg Leu Leu Ala
            385             390             395

GGC CTC TTC CCC TAC ATC ACC TCG GAG GAG CGC CAG GCC GTC GCG AAG     1249
Gly Leu Phe Pro Tyr Ile Thr Ser Glu Glu Arg Gln Ala Val Ala Lys
            400             405             410

CAG TAC CCG ATC TCC GAC GCG CCG TCA AAG GGC AAC ACC TTC TCT CGC     1297
Gln Tyr Pro Ile Ser Asp Ala Pro Ser Lys Gly Asn Thr Phe Ser Arg
    415             420             425

ATC TCG GCC GTC ATC GCG GAC TCG ACC TTC GTC TGC CCG ACC TAC TGG     1345
Ile Ser Ala Val Ile Ala Asp Ser Thr Phe Val Cys Pro Thr Tyr Trp
430             435             440             445

ACC GCC GAG GCG TTC GGC TCG TCC GCC CAC AAG GGC CTC TTC GAC TAC     1393
Thr Ala Glu Ala Phe Gly Ser Ser Ala His Lys Gly Leu Phe Asp Tyr
            450             455             460

GCG CCG GCT CAC CAC GCG ACC GAC AAC TCG TAC TAC ATC GGC TCC ATC     1441
Ala Pro Ala His His Ala Thr Asp Asn Ser Tyr Tyr Ile Gly Ser Ile
            465             470             475

TGG AAC GGC AAG AAG TCG GTC TCG TCC GTC CAG TCC TTC GAC GGC GCG     1489
Trp Asn Gly Lys Lys Ser Val Ser Ser Val Gln Ser Phe Asp Gly Ala
            480             485             490

CTC GGC GGC TTC ATC GAG ACG TTC AAC CCG AAC AAC AAC GCT GCC AAC     1537
Leu Gly Gly Phe Ile Glu Thr Phe Asn Pro Asn Asn Asn Ala Ala Asn
    495             500             505

AAG ACC ATC AAC CCT TAC TGG CCG ACG TTC GAC TCG GGC AAG CAG CTC     1585
Lys Thr Ile Asn Pro Tyr Trp Pro Thr Phe Asp Ser Gly Lys Gln Leu
510             515             520             525

CTC TTC AAC ACG ACG ACG AGG GAC ACC CTC TCT CCC GCC GAC CCG CGC     1633
Leu Phe Asn Thr Thr Thr Arg Asp Thr Leu Ser Pro Ala Asp Pro Arg
            530             535             540

ATC GTT GAG ACT TCA AGC TTG ACC GAC TTT GGC ACG AGC CAG AAG ACC     1681
Ile Val Glu Thr Ser Ser Leu Thr Asp Phe Gly Thr Ser Gln Lys Thr
            545             550             555

AAG TGC GAC TTC TGG CGT GGG TCA ATC TCG GTG AAC GCG GGT CTC         1726
Lys Cys Asp Phe Trp Arg Gly Ser Ile Ser Val Asn Ala Gly Leu
            560             565             570

TAGGCGTCTT TC                                                       1738
```

( 2 ) INFORMATION FOR SEQ ID NO:2:

-continued (i) SEQUENCE CHARACTERISTICS:
    (A) LENGTH: 572 amino acids
    (B) TYPE: amino acid
    (D) TOPOLOGY: linear (ii) MOLECULE TYPE: protein (xi) SEQUENCE DESCRIPTION: SEQ ID NO:2:

```
Met Leu Leu Asn Leu Phe Thr Leu Ala Ser Leu Ala Ala Thr Leu Gln
 1               5                  10                  15

Leu Ala Phe Ala Ser Pro Thr Ser Leu Val Arg Arg Thr Asn Pro Asn
                20                  25                  30

Glu Pro Pro Pro Val Val Asp Leu Gly Tyr Ala Arg Tyr Gln Gly Tyr
            35                  40                  45

Leu Asn Glu Thr Ala Gly Leu Tyr Trp Trp Arg Gly Ile Arg Tyr Ala
        50                  55                  60

Ser Ala Gln Arg Phe Gln Ala Pro Gln Thr Pro Ala Thr His Lys Ala
 65                  70                  75                  80

Val Arg Asn Ala Thr Glu Tyr Gly Pro Ile Cys Trp Pro Ala Ser Glu
                85                  90                  95

Gly Thr Asn Thr Thr Lys Gly Leu Pro Pro Pro Ser Asn Ser Ser Ser
               100                 105                 110

Ser Ala Pro Gln Lys Gln Ala Ser Glu Asp Cys Leu Phe Leu Asn Val
           115                 120                 125

Val Ala Pro Ala Gly Ser Cys Glu Gly Asp Asn Leu Pro Val Leu Val
       130                 135                 140

Tyr Ile His Gly Gly Gly Tyr Ala Phe Gly Asp Ala Ser Thr Gly Ser
145                 150                 155                 160

Asp Phe Ala Ala Phe Thr Lys His Thr Gly Thr Lys Met Val Val Val
               165                 170                 175

Asn Leu Gln Tyr Arg Leu Gly Ser Phe Gly Phe Leu Ala Gly Gln Ala
           180                 185                 190

Met Lys Asp Tyr Gly Val Thr Asn Ala Gly Leu Leu Asp Gln Gln Phe
       195                 200                 205

Ala Leu Gln Trp Val Gln Gln His Val Ser Lys Phe Gly Gly Asn Pro
   210                 215                 220

Asp His Val Thr Ile Trp Gly Glu Ser Ala Gly Ala Gly Ser Val Met
225                 230                 235                 240

Asn Gln Ile Ile Ala Asn Gly Gly Asn Thr Val Lys Ala Leu Gly Leu
               245                 250                 255

Lys Lys Pro Leu Phe His Ala Ala Ile Gly Ser Ser Val Phe Leu Pro
           260                 265                 270

Tyr Gln Ala Lys Tyr Asn Ser Pro Phe Ala Glu Leu Leu Tyr Ser Gln
       275                 280                 285

Leu Val Ser Ala Thr Asn Cys Thr Lys Ala Ala Ser Ser Phe Ala Cys
   290                 295                 300

Leu Glu Ala Val Asp Ala Ala Leu Ala Ala Ala Gly Val Lys Asn
305                 310                 315                 320

Ser Ala Ala Phe Pro Phe Gly Phe Trp Ser Tyr Val Pro Val Val Asp
           325                 330                 335

Gly Thr Phe Leu Thr Glu Arg Ala Ser Leu Leu Leu Ala Lys Gly Lys
       340                 345                 350

Lys Asn Leu Asn Gly Asn Leu Phe Thr Gly Ile Asn Asn Leu Asp Glu
   355                 360                 365

Gly Phe Ile Phe Thr Asp Ala Thr Ile Gln Asn Asp Thr Ile Ser Asp
370                 375                 380
```

| | | | | | | | | | | | | | | |
|---|---|---|---|---|---|---|---|---|---|---|---|---|---|---|
| Gln | Ser | Gln | Arg | Val | Ser | Gln | Phe | Asp | Arg | Leu | Leu | Ala | Gly | Leu | Phe |
| 385 | | | | | 390 | | | | | 395 | | | | | 400 |
| Pro | Tyr | Ile | Thr | Ser | Glu | Glu | Arg | Gln | Ala | Val | Ala | Lys | Gln | Tyr | Pro |
| | | | | 405 | | | | | 410 | | | | | 415 | |
| Ile | Ser | Asp | Ala | Pro | Ser | Lys | Gly | Asn | Thr | Phe | Ser | Arg | Ile | Ser | Ala |
| | | | 420 | | | | | 425 | | | | | 430 | | |
| Val | Ile | Ala | Asp | Ser | Thr | Phe | Val | Cys | Pro | Thr | Tyr | Trp | Thr | Ala | Glu |
| | | 435 | | | | | 440 | | | | | 445 | | | |
| Ala | Phe | Gly | Ser | Ser | Ala | His | Lys | Gly | Leu | Phe | Asp | Tyr | Ala | Pro | Ala |
| | 450 | | | | | 455 | | | | | 460 | | | | |
| His | His | Ala | Thr | Asp | Asn | Ser | Tyr | Tyr | Ile | Gly | Ser | Ile | Trp | Asn | Gly |
| 465 | | | | | 470 | | | | | 475 | | | | | 480 |
| Lys | Lys | Ser | Val | Ser | Ser | Val | Gln | Ser | Phe | Asp | Gly | Ala | Leu | Gly | Gly |
| | | | | 485 | | | | | 490 | | | | | 495 | |
| Phe | Ile | Glu | Thr | Phe | Asn | Pro | Asn | Asn | Asn | Ala | Ala | Asn | Lys | Thr | Ile |
| | | | 500 | | | | | 505 | | | | | 510 | | |
| Asn | Pro | Tyr | Trp | Pro | Thr | Phe | Asp | Ser | Gly | Lys | Gln | Leu | Leu | Phe | Asn |
| | | 515 | | | | | 520 | | | | | 525 | | | |
| Thr | Thr | Thr | Arg | Asp | Thr | Leu | Ser | Pro | Ala | Asp | Pro | Arg | Ile | Val | Glu |
| | 530 | | | | | 535 | | | | | 540 | | | | |
| Thr | Ser | Ser | Leu | Thr | Asp | Phe | Gly | Thr | Ser | Gln | Lys | Thr | Lys | Cys | Asp |
| 545 | | | | | 550 | | | | | 555 | | | | | 560 |
| Phe | Trp | Arg | Gly | Ser | Ile | Ser | Val | Asn | Ala | Gly | Leu | | | | |
| | | | | 565 | | | | | 570 | | | | | | |

( 2 ) INFORMATION FOR SEQ ID NO:3:

( i ) SEQUENCE CHARACTERISTICS:
        ( A ) LENGTH: 2220 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

```
GGATCCACCC GAACTCTGTC CCGCTTTCTG GCTTTCTTCC TTGCTGTCGC CCCATCGCCT      60
TTCCCGACTC GCCGCCATGC TCCTTAACCT CTTCACCCTC GCCTCCCTCG CTGCGACGCT     120
CCAGCTCGCC TTTGCCTCTC CGACCTCCCT CGTCCGCCGC ACGAACCCAA ACGAGCCCCC     180
TCCCGTCGTC GACCTCGGCT ACGCCCGCTA CCAAGGCTAC TTGAACGAGA CCGCCGGACT     240
CTACTGGTGG CGCGGAATCC GCTACGCCTC GGCTCAGCGC TTCCAGGCTC CTCAGACGCC     300
CGCGACGCAC AAGGCCGTCC GCAACGCGAC TGAGTATGGA CCGATCTGTT GGCCGGCTAG     360
CGAGGGAACC AACACGACCA AGGGCTTGCC GCCGCCTAGC AACAGCTCGA GCAGCGCGCC     420
GCAGAAACAG GCGTCGGAGG ATTGCCTCTT CCTCAATGTC GTTGCCCCCG CCGGCTCGTG     480
CGAGGGCGAC AATCTTCCCG TCCTCGTCTA CATTCACGGA GGTGGCTACG CCTTCGGCGA     540
TGCGAGCACC GGCAGCGACT TTGCCGCCTT CACCAAGCAC ACGGGAACCA AGATGGTCGT     600
TGTAAATCTC CAGTACCGTC TCGGCAGCTT TGGTTTCCTC GCTGGCCAAG CCATGAAGGA     660
CTACGGTGTA ACGAACGCCG GCTTGCTTGA CCAGGTGAGT TTCCCGCATG ATACCCGCCC     720
ACCTTTCGAC TCATGCTGAC GCCTCTCCCG CTCGCAGCAA TTCGCCCTTC AATGGGTTCA     780
ACAGCACGTC TCGAAGTTCG GCGGCAACCC CGATCACGTT ACGATTTGGG GCGAGTCTGC     840
AGGCGCAGGG TCCGTTATGA ACCAGATCAT TGCGAACGTG AGCCACCCGA ACCGATCTCC     900
```

-continued

| | | | | | |
|---|---|---|---|---|---|
| AGCCGACTTT | CCCCCCCCCC | CCCCCCCCGC | TGACCTCCCT | CGTCTTGCAG | GGCGGCAACA | 960 |
| CCGTCAAGGC | TCTCGGTCTC | AAGAAGCCCC | TCTTCCACGC | TGCCATCGGC | TCCTCCGTCT | 1020 |
| TCCTCCCCTA | CCAAGCCAAG | TACAACTCCC | CCTTCGCCGA | GCTGCTCTAC | TCCCAACTCG | 1080 |
| TCTCGGCGAC | AAACTGCACC | AAAGCCGCCT | CGTCCTTCGC | TTGCCTCGAA | GCTGTCGACG | 1140 |
| CTGCGGCGCT | CGCTGCGGCG | GGCGTGAAGA | ACTCGGCGGC | GTTCCCGTTC | GGGTTTTGGT | 1200 |
| CGTATGTCCC | GGTCGTCGAC | GGGACCTTCT | TGACTGAGCG | CGCGTCGCTC | CTTCTCGCCA | 1260 |
| AGGGCAAGAA | GAACCTCAAT | GGCGTGCGTG | GCGAGCTTTC | GAGTGCTTCA | GGATCTCGCT | 1320 |
| GACACTGTCG | ACCGGCTCGC | AGAACCTCTT | CACCGGGATC | AACAACCTCG | ACGAAGATGA | 1380 |
| GTTCCCGTCG | ACGGCTCTGT | TCGCCCAGCG | AGACTGACTT | GTTCTTTTGC | GAAGATTACG | 1440 |
| ATTCATATTC | ACTGACGCCA | CTATTCAGAA | CGACACGATC | AGCGACCAGT | CGCAGCGCGT | 1500 |
| CTCCAGTTC | GACCGCCTCC | TCGCCGGCCT | CTTCCCCTAC | ATCACCTCGG | AGGAGCGCCA | 1560 |
| GGCCGTCGCG | AAGCAGTACC | CGATCTCCGA | CGCGCCGTCA | AAGGGCAACA | CCTTCTCTCG | 1620 |
| CATCTCGGCC | GTCATCGCGG | ACTCGACCTT | CGTGTGCGTT | CCCCGTCGTC | TTCTCCGAGT | 1680 |
| ATTCCGCTGA | CTTCCCGCTT | GCCCGCAGCT | GCCCGACCTA | CTGGACCGCC | GAGGCGTTCG | 1740 |
| GCTCGTCCGC | CCACAAGGGC | CTCTTCGACT | ACGCGCCGGC | TCACCACGCG | ACCGACAACT | 1800 |
| CGTACTACAT | CGGCTCCATC | TGGAACGGCA | AGAAGTCGGT | CTCGTCCGTC | CAGTCCTTCG | 1860 |
| ACGGCGCGCT | CGGCGGCTTC | ATCGAGACGT | TCAACCCGAA | CAACAACGCT | GCCAACAAGA | 1920 |
| CCATCAACCC | TTACTGGCCG | ACGTTCGACT | CGGGCAAGCA | GCTCCTCTTC | AACACGACGA | 1980 |
| CGAGGGACAC | CCTCTCTCCC | GCCGACCCGC | GCATCGTTGA | GACTTCAAGC | TTGACCGACT | 2040 |
| TTGGCACGAG | CCAGAAGACC | AAGTGCGACT | TCTGGCGTGG | GTCAATCTCG | GTGAACGCGG | 2100 |
| GTCTCTAGGC | GTCTTTCCTT | CCGACTTCCT | TCGTTCTTTC | GTTGTTTATT | CTTGCAGTTC | 2160 |
| CGTTGTATCG | GCCATTCGTG | CGTGTAGCTC | ACTCGAGTAT | AGACGTTGGC | AAGTGCGAAA | 2220 |

( 2 ) INFORMATION FOR SEQ ID NO:4:

( i ) SEQUENCE CHARACTERISTICS:
        ( A ) LENGTH: 544 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:4:

```
Thr Asn Pro Asn Glu Pro Pro Pro Val Val Asp Leu Gly Tyr Ala Arg
 1               5                  10                  15

Tyr Gln Gly Tyr Leu Asn Glu Thr Ala Gly Leu Tyr Trp Trp Arg Gly
            20                  25                  30

Ile Arg Tyr Ala Ser Ala Gln Arg Phe Gln Ala Pro Gln Thr Pro Ala
        35                  40                  45

Thr His Lys Ala Val Arg Asn Ala Thr Glu Tyr Gly Pro Ile Cys Trp
    50                  55                  60

Pro Ala Ser Glu Gly Thr Asn Thr Thr Lys Gly Leu Pro Pro Pro Ser
65                  70                  75                  80

Asn Ser Ser Ser Ser Ala Pro Gln Lys Gln Ala Ser Glu Asp Cys Leu
                85                  90                  95

Phe Leu Asn Val Val Ala Pro Ala Gly Ser Cys Glu Gly Asp Asn Leu
            100                 105                 110

Pro Val Leu Val Tyr Ile His Gly Gly Gly Tyr Ala Phe Gly Asp Ala
        115                 120                 125
```

```
Ser  Thr  Gly  Ser  Asp  Phe  Ala  Ala  Phe  Thr  Lys  His  Thr  Gly  Thr  Lys
     130                 135                      140
Met  Val  Val  Val  Asn  Leu  Gln  Tyr  Arg  Leu  Gly  Ser  Phe  Gly  Phe  Leu
145                      150                      155                      160
Ala  Gly  Gln  Ala  Met  Lys  Asp  Tyr  Gly  Val  Thr  Asn  Ala  Gly  Leu  Leu
                    165                      170                      175
Asp  Gln  Gln  Phe  Ala  Leu  Gln  Trp  Val  Gln  Gln  His  Val  Ser  Lys  Phe
               180                      185                      190
Gly  Gly  Asn  Pro  Asp  His  Val  Thr  Ile  Trp  Gly  Glu  Ser  Ala  Gly  Ala
          195                      200                      205
Gly  Ser  Val  Met  Asn  Gln  Ile  Ile  Ala  Asn  Gly  Gly  Asn  Thr  Val  Lys
     210                      215                      220
Ala  Leu  Gly  Leu  Lys  Lys  Pro  Leu  Phe  His  Ala  Ala  Ile  Gly  Ser  Ser
225                      230                      235                      240
Val  Phe  Leu  Pro  Tyr  Gln  Ala  Lys  Tyr  Asn  Ser  Pro  Phe  Ala  Glu  Leu
                    245                      250                      255
Leu  Tyr  Ser  Gln  Leu  Val  Ser  Ala  Thr  Asn  Cys  Thr  Lys  Ala  Ala  Ser
               260                      265                      270
Ser  Phe  Ala  Cys  Leu  Glu  Ala  Val  Asp  Ala  Ala  Ala  Leu  Ala  Ala  Ala
          275                      280                      285
Gly  Val  Lys  Asn  Ser  Ala  Ala  Phe  Pro  Phe  Gly  Phe  Trp  Ser  Tyr  Val
     290                      295                      300
Pro  Val  Val  Asp  Gly  Thr  Phe  Leu  Thr  Glu  Arg  Ala  Ser  Leu  Leu  Leu
305                      310                      315                      320
Ala  Lys  Gly  Lys  Lys  Asn  Leu  Asn  Gly  Asn  Leu  Phe  Thr  Gly  Ile  Asn
                    325                      330                      335
Asn  Leu  Asp  Glu  Gly  Phe  Ile  Phe  Thr  Asp  Ala  Thr  Ile  Gln  Asn  Asp
               340                      345                      350
Thr  Ile  Ser  Asp  Gln  Ser  Gln  Arg  Val  Ser  Gln  Phe  Asp  Arg  Leu  Leu
          355                      360                      365
Ala  Gly  Leu  Phe  Pro  Tyr  Ile  Thr  Ser  Glu  Glu  Arg  Gln  Ala  Val  Ala
     370                      375                      380
Lys  Gln  Tyr  Pro  Ile  Ser  Asp  Ala  Pro  Ser  Lys  Gly  Asn  Thr  Phe  Ser
385                      390                      395                      400
Arg  Ile  Ser  Ala  Val  Ile  Ala  Asp  Ser  Thr  Phe  Val  Cys  Pro  Thr  Tyr
                    405                      410                      415
Trp  Thr  Ala  Glu  Ala  Phe  Gly  Ser  Ser  Ala  His  Lys  Gly  Leu  Phe  Asp
               420                      425                      430
Tyr  Ala  Pro  Ala  His  His  Ala  Thr  Asp  Asn  Ser  Tyr  Tyr  Ile  Gly  Ser
          435                      440                      445
Ile  Trp  Asn  Cys  Lys  Lys  Ser  Val  Ser  Ser  Val  Gln  Ser  Phe  Asp  Gly
     450                      455                      460
Ala  Leu  Gly  Gly  Phe  Ile  Glu  Thr  Phe  Asn  Pro  Asn  Asn  Ala  Ala
465                      470                      475                      480
Asn  Lys  Thr  Ile  Asn  Pro  Tyr  Trp  Pro  Thr  Phe  Asp  Ser  Gly  Lys  Gln
                    485                      490                      495
Leu  Leu  Phe  Asn  Thr  Thr  Thr  Arg  Asp  Thr  Leu  Ser  Pro  Ala  Asp  Pro
               500                      505                      510
Arg  Ile  Val  Glu  Thr  Ser  Ser  Leu  Thr  Asp  Phe  Gly  Thr  Ser  Gln  Lys
          515                      520                      525
Thr  Lys  Cys  Asp  Phe  Trp  Arg  Gly  Ser  Ile  Ser  Val  Asn  Ala  Gly  Leu
     530                      535                      540
```

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:5:

GGYTCRTTGG GRTTNGT      17

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:6:

GGYTCRTTAG GRTTNGT      17

( 2 ) INFORMATION FOR SEQ ID NO:7:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:7:

GGYTCRTTTG GRTTNGT      17

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:8:

GGYTCRTTCG GRTTNGT      17

( 2 ) INFORMATION FOR SEQ ID NO:9:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

Thr Asn Pro Asn Glu Pro
    1                5

( 2 ) INFORMATION FOR SEQ ID NO:10:

( i ) SEQUENCE CHARACTERISTICS:
        ( A ) LENGTH: 17 base pairs ( B ) TYPE: nucleic acid
            ( C ) STRANDEDNESS: single
            ( D ) TOPOLOGY: linear ( i i ) MOLECULE TYPE: other nucleic acid ( x i ) SEQUENCE DESCRIPTION: SEQ ID NO:10:

ACNAAYCCNA AYGARCC                                                                                          17

( 2 ) INFORMATION FOR SEQ ID NO:11:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( i i ) MOLECULE TYPE: other nucleic acid ( x i ) SEQUENCE DESCRIPTION: SEQ ID NO:11:

GGYTCRTTNG GRTTNGT                                                                                          17

CEPHALOSPORIN ESTERASE GENE FROM *RHODOSPORIDIUM TORULOIDES*

CROSS REFERENCE TO RELATED APPLICATION

This application claims the benefit of provisional application Ser. No. 60/026,929 filed Sep. 18, 1996.

FIELD OF THE INVENTION

The present invention concerns isolated cephalosporin esterase from *Rhodosporidium toruloides* and nucleic acids encoding said esterase.

BACKGROUND OF THE INVENTION

Cephalosporin esterase is a general term for an enzyme which is capable of hydrolyzing the 3' acetyl group of cephalosporins of the general structure I to its corresponding desacetyl compound II.

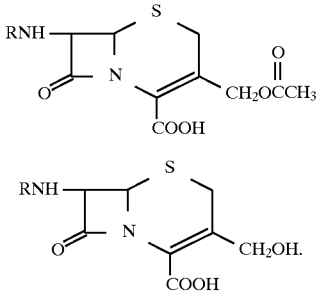

Chemical deacetylation of cephalosporins is performed under extreme pH conditions which generally tend to give side products in addition to the desired desacetyl compound. Enzymatic deacetylation has been described in a number of journal articles and patents. The cephalosporin C esterase activity of the pink yeast *Rhodosporidium toruloides* was first reported by Smith et al. at Glaxo Laboratories U.S. Pat. No. 4,533,632 and was used in U.S. Pat. No. 5,512,454. However, whole cells or crude extracts were used for the conversion and the enzyme was not purified and characterized.

Heretofore, isolated cephalosporin esterase from *Rhodosporidium toruloides* and nucleic acids encoding the esterase has been unknown.

SUMMARY OF THE INVENTION

The present invention is directed to isolated and purified cephalosporin esterase from *Rhodosporidium toruloides* preferably having the sequence of SEQ. I.D. NOS.: 2 or 4. SEQ. ID. NO.: 2 is the amino acid sequence of the entire or intact esterase whereas SEQ. ID. NO.: 4 is the sequence of the mature peptide which is a 544 amino acid fragment of the intact esterase with the first (N-terminal) 28 amino acids cleaved off. The cleavage of the first 28 amino acids occurs in some host cells, for example *E.Coli*. The mature peptide typically exhibits better enzymatic activity than the intact esterase.

The present invention is also directed to nucleic acids coding for the esterase, preferably the cDNA of SEQ. I.D. NO.:1 or the genomic DNA of SEQ. I.D. No.:3.

BRIEF DESCRIPTION OF THE DRAWINGS

FIG. 4 The N-terminus of the protein (SEQ. I.D. NO.:9), the reverse translation sequence of the genomic N-terminus (SEQ. ID. NO.: 10), the inverse translation sequence that is complementary to the reverse translation sequence (SEQ. ID. NO.: 11), and the four oligonucleotide probes (Probes 1–4, SEQ. I.D. NOS.: 5–8, respectively) used to identify the gene for the esterase. X represents any nucleotide FIG. 5a The cDNA sequence coding for the esterase of the invention (SEQ. I.D. NO.:1) and the corresponding amino acid sequence of the esterase of the invention (SEQ. I.D. NO.:2).

FIG. 5b Continuation of FIG. 5a.

FIG. 6a The genomic DNA sequence coding for the esterase of the invention (SEQ. I.D. NO.:3) and the corresponding amino acid sequence of the esterase of the invention (SEQ. I.D. NO.:2).

FIG. 6b Continuation of FIG. 6a.

FIG. 7 The amino acid sequence of the esterase of the invention containing 572 amino acids (SEQ. ID. NO.: 2) showing the 551 amino acid sequence of the mature peptide (SEQ. ID. NO.: 4) which typically has better enzymatic activity than the entire protein.

FIG. 8 Analysis of the amino acid composition of the intact esterase of the invention.

DETAILED DESCRIPTION OF THE INVENTION

Figure 1:
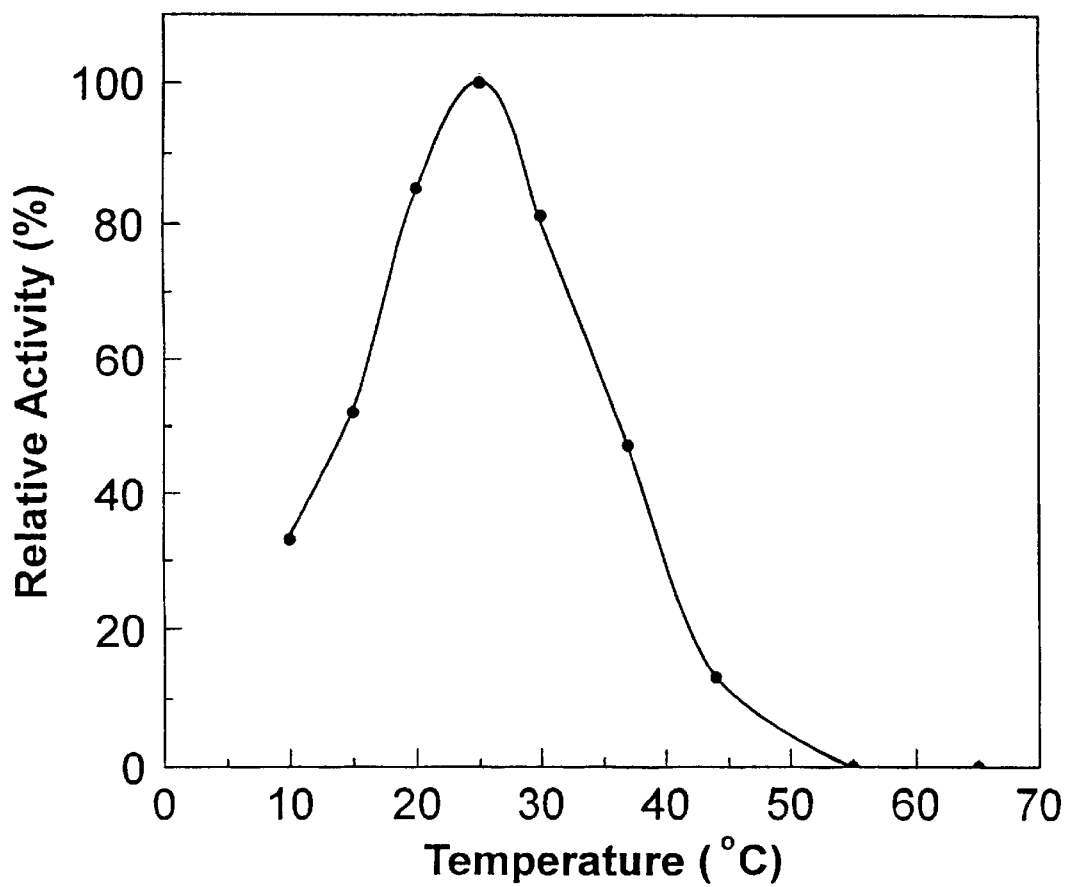
FIG. 1 Optimum temperature of the cephalosporin esterase.

The present invention concerns an isolated nucleic acid molecule comprising a nucleic acid sequence coding for all or part of cephalosporin esterase from *Rhodosporidium toruloides*. A preferred strain of *Rhodospordium toruloides* is ATCC 10657 which is well known in the art and is deposited with and available from the American Type Culture Collection, 10801 University Boulevard, Manassas, Va. 20110-2209 and is described in U.S. Pat. No. 4,533,632. Preferably, the nucleic acid molecule is a DNA molecule and the nucleic acid sequence is a DNA sequence. All DNA sequences are represented herein by formulas whose left to right orientation is in the conventional direction of 5' to 3'. Nucleotide base abbreviations used herein are conventional in the art, i.e., T is thymine, A is adenine, C is cytosine, and G is guanine; also, X is A,T,C, or G, Pu is purine (i.e., G or A), and Py is pyrimidine (i.e., T or G). Further preferred is a DNA sequence having all or part of the nucleotide sequence substantially as shown in FIGS. 5 and 6; or a DNA sequence complementary to one of these DNA sequences; or a DNA sequence which hybridizes to a DNA sequence complementary to one of these DNA sequences. Preferably, the DNA sequence hybridizes under stringent conditions. Stringent hybridization conditions select for DNA sequences of greater than 80% homology, preferably greater than 85% or, more preferably, greater than 90% homology. Screening DNA under stringent conditions may be carried out according to the method described in *Nature*, 313: 402–404 (1985). The DNA sequences capable of hybridizing under stringent conditions with the DNA disclosed in the present application may be, for example, allelic variants of the disclosed DNA sequences, may be naturally present in *Rhodosporidium toluloides* but related to the disclosed DNA sequences, or may be derived from other bacterial sources. General techniques of nucleic acid hybridization are disclosed by Maniatis, T. et al., In: *Molecular Cloning, a Laboratory Manual*, Cold Spring Harbor, N.Y. (19820, and by Haymes, B. D. et al., In: *Nucleic Acid Hybridization, a Practical Approach*, IRL Press, Washington, D.C. (1985), which references are incorporated herein by reference. In the case of a nucleotide sequence (e.g., a DNA sequence) coding for part of cephalosporin esterase, it is preferred that the nucleotide sequence be at least about 20 nucleotides in length.

Preferred DNA fragments are the probes of SEQ. ID. NOS.:5–8.

The cephalosporin esterase molecules of the present invention do not necessarily need to be catalytically active. For example, catalytically inactive cephalosporin esterase or fragments thereof may be useful in raising antibodies to the protein.

It is also contemplated that the present invention encompasses modified sequences. As used in the present application, the term "modified", when referring to a nucleotide or polypeptide sequence, means a nucleotide or polypeptide sequence which differs from the wild-type sequence found in nature.

The DNA sequences of the present invention can be obtained using various methods well-known to those of ordinary skill in the art. At least three alternative principal methods may be employed:

(i) the isolation of a double-stranded DNA sequence from genomic DNA or complementary DNA (cDNA) which contains the sequence;

(2) the chemical synthesis of the DNA sequence; and (3) the synthesis of the DNA sequence by polymerase chain reaction (PCR).

In the first approach, a genomic or cDNA library can be screened in order to identify a DNA sequence coding for all or part of cephalosporin esterase. For example, a *R. toruloides* genomic DNA library can be screened in order to identify the DNA sequence coding for all or part of cephalosporin esterase. Various techniques can be used to screen the genomic DNA or cDNA libraries.

For example, labeled single stranded DNA probe sequences duplicating a sequence present in the target genomic DNA or cDNA coding for all or part of cephalosporin esterase can be employed in DNA/DNA hybridization procedures carried out on cloned copies of the genomic DNA or cDNA which have been denatured to single stranded form.

A genomic DNA or cDNA library can also be screened for a genomic DNA or cDNA coding for all or part of cephalosporin esterase using immunoblotting techniques.

In one typical screening method suitable for either immunoblotting or hybridization techniques, the genomic DNA library, which is usually contained in a vector, or cDNA library is first spread out on agar plates, and then the clones are transferred to filter membranes, for example, nitrocellulose membranes. A DNA probe can then be hybridized or an antibody can then be bound to the clones to identify those clones containing the genomic DNA or cDNA coding for all or part of cephalosporin esterase.

In the second approach, the DNA sequences of the present invention coding for all or part of cephalosporin esterase can be chemically synthesized. For example, the DNA sequence coding for cephalosporin esterase can be synthesized as a series of 100 base oligonucleotides that can be sequentially ligated (via appropriate terminal restriction sites or complementary terminal sequences) so as to form the correct linear sequence of nucleotides.

In the third approach, the DNA sequences of the present invention coding for all or part of cephalosporin esterase can be synthesized using PCR. Briefly, pairs of synthetic DNA oligonucleotides at least 15 bases in length (PCR primers) that hybridize to opposite strands of the target DNA sequence are used to enzymatically amplify the intervening region of DNA on the target sequence. Repeated cycles of heat denaturation of the template, annealing of the primers and extension of the 3'-termini of the annealed primers with a DNA polymerase results in amplification of the segment defined by the 5' ends of the PCR primers. See, White et al., Trends Genet. 5, 185–189 (1989).

The DNA sequences of the present invention can be used in a variety of ways in accordance with the present invention. The most apparent use of the DNA sequence is to prepare cephalosporin esterase to be useful for the hydrolysis of the 3' acetyl groups of cephalosporins. However, they also can be used as DNA probes to screen other cDNA and genomic DNA libraries as to select by hybridization other DNA sequences that code for proteins related to cephalosporin esterase. In addition, the DNA sequences of the present invention coding for all or part of cephalosporin esterase can be used as DNA probes to screen other cDNA and genomic DNA libraries to select by hybridization DNA sequences that code for cephalosporin esterase molecules from organisms other than *R. toruloides*.

The DNA sequences of the present invention coding for all or part of cephalosporin esterase can also be modified (i.e., mutated) to prepare various mutations. Such mutations may be either degenerate, i.e., the mutation changes the amino acid sequence encoded by the mutated codon, or non-degenerate, i.e., the mutation does not change the amino acid sequence encoded by the mutated codon. These modified DNA sequences may be prepared, for example, by mutating the cephalosporin esterase DNA sequence so that the mutation results in the deletion, substitution, insertion, inversion or addition of one or more amino acids in the encoded polypeptide using various methods known in the art. For example, the methods of site-directed mutagenesis described in Morinaga et al., Bio/Technol. 2, 636–639 (1984), Taylor et al., Nucl. Acids Res. 13, 8749–8764 (1985) and Kunkel, Proc. Natl. Acad. Sci. USA 82, 482–492 (1985) may be employed. In addition, kits for site-directed mutagenesis may be purchased from commercial vendors. For example, a kit for performing site-directed mutagenesis may be purchased from Amersham Corp. (Arlington Heights, Ill.). In addition, disruption, deletion and truncation methods as described in Sayers et al., Nucl. Acids Res. 16, 791–802 (1988) may also be employed. Both degenerate and non-degenerate mutations may be advantageous in producing or using the polypeptides of the present invention. For example, these mutations may permit higher levels of production, easier purification, or provide additional restriction endonuclease recognition sites. All such modified DNA and polypeptide molecules are included within the scope of the present invention.

The present invention further concerns expression vectors comprising a DNA sequence coding for all or part of cephalosporin esterase. The expression vectors preferably contain all or part of one of the DNA sequences having the nucleotide sequences substantially as shown in FIGS. 6 or 7. Further preferred are expression vectors comprising one or more regulatory DNA sequences operatively linked to the DNA sequence coding for all or part of cephalosporin esterase. As used in this context, the term "operatively linked" means that the regulatory DNA sequences are capable of directing the replication and/or the expression of the DNA sequence coding for all or part of cephalosporin esterase.

Expression vectors of utility in the present invention are often in the form of "plasmids", which refer to circular double stranded DNA loops which, in their vector form, are not bound to the chromosome. However, the invention is intended to include such other forms of expression vectors which serve equivalent functions and which become known in the art subsequently hereto.

Expression vectors useful in the present invention typically contain an origin of replication, a promoter located in front (i.e., upstream of) the DNA sequence and followed by the DNA sequence coding for all or part of the structural protein. The DNA sequence coding for all or part of the structural protein is followed by transcription termination sequences and the remaining vector. The expression vectors may also include other DNA sequences known the art, for example, stability leader sequences which provide for stability of the expression product, secretory leader sequences which provide for secretion of the expression product, sequences which allow expression of the structural gene to modulated (e.g., by the presence or absence of nutrients or other inducers in the growth medium), marking sequences which are capable of providing phenotypic selection in transformed host cells, stability elements such as centromeres which provide mitotic stability to the plasmid, and sequences which provide sites for cleavage by restriction endonucleases. The characteristics of the actual expression vector used must be compatible with the host cell which is to be employed. For example, when cloning in a fungal cell system, the expression vector should contains promoters isolated from the genome of fungal cells (e.g., the cephalosporin esterase promoter from *R. toruloides* or the trpC promoter from *Aspergillus nidulans*). Certain expression vectors may contain a fungal autonomously replicating sequence (ARS; e.g., ARS from *Fusarium oxysporum* and *Saccharomyces cerevisiae*) which promotes in vivo production of self-replicating plasmids in fungal hosts. It is preferred that the fungal expression vectors of the invention do not have a fungal ARS sequence and thus will integrate into host chromosomes upon plasmid entry of host cells. Such integration is preferred because of enhanced genetic stability. An expression vector as contemplated by the present invention is at least capable of directing the replication in *Escherichia coli* and integration in fungal cells, and preferably the expression, of the cephalosporin esterase DNA sequences of the present invention. Suitable origins of replication in *E. coli* various hosts include, for example, a ColE1 plasmid replication origin. Suitable promoters include, for example, the trpC promoter from *A. nidulans* and the neo-r gene promoter from *E coli*. Suitable termination sequences include, for example, the trpC terminator from *A. nidulans*, and the neo-r gene terminator from *E. coli*. It is also preferred that the expression vector include a sequence coding for a selectable marker. The selectable marker is preferably antibiotic resistance. As selectable markers, phleomycin resistance (for fungal cells), ampicillin resistance, and neomycin resistance (for bacterial cells) can be conveniently employed. All of these materials are known in the art and are commercially available.

Suitable expression vectors containing the desired coding and control sequences may be constructed using standard recombinant DNA techniques known in the art, many of which are described in Sambrook et al. Molecular Cloning: A Laboratory Manual, 2nd edition, Cold Spring Harbor Laboratory, Cold Spring Harbor, N.Y. (1989).

The present invention additionally concerns host cells containing an expression vector which comprises a DNA sequence coding for all or part of cephalosporin esterase. The host cells preferably contain an expression vector which comprises all or one of the DNA sequence having the nucleotide sequences substantially as shown in FIGS. 6 or 7. Further preferred are host cells containing an expression vector comprising one or more regulatory DNA sequences capable of directing the replication and/or the expression of and operatively linked to a DNA sequence coding for all or part of cephalosporin esterase. Additionally included are host cells containing an expression vector which comprises a DNA sequence which has been modified (e.g., disrupted, deleted or truncated) so as to code for a cephalosporin esterase molecule which is not catalytically active. Suitable host cells include both eukaryotic and prokaryotic host cells, for example, *E. coli* cells. Suitable eukaryotic host cells include, for example, *R. toruloides, Cephalosporium acremonium*, and *Penicillium chrysogenum* cells.

Expression vectors may be introduced into host cells by various methods known in the art. For example, transfection of host cells with expression vectors can be carried out by the polyethylene glycol mediated protoplast transformation method. However, other methods for introducing expression vectors into host cells, for example, electroporation, biolistic injection, or protoplast fusion, can also be employed.

Once an expression vector has been introduced into an appropriate host cell, the host cell may be cultured under conditions permitting expression of large amounts of the desired polypeptide, in the preferred case a polypeptide molecule comprising all or part of cephalosporin esterase.

Host cells containing an expression vector which contains a DNA sequence coding for all or part of cephalosporin esterase may be identified by one or more of the following six general approaches: (a) DNA—DNA hybridization; (b) the presence or absence of marker gene functions; (d) assessing the level of transcription as measured by the production of cephalosporin esterase mRNA transcripts in the host cell; (d) detection of the gene product immunologically; (e) calorimetric detection; and (f) enzyme assay, enzyme assay being the preferred method of identification.

In the first approach, the presence of a DNA sequence coding for all or part of cephalosporin esterase can be detected by DNA—DNA or RNA-DNA hybridization using probes complementary to the DNA sequence.

In the second approach, the recombinant expression vector host system can be identified and selected based upon the presence or absence of certain marker gene functions (e.g., acetamide utilization, resistance to antibiotics, resistance to fungicide, uracil prototrophy, etc.). A marker gene can be placed in the same plasmid as the DNA sequence coding for all or part of cephalosporin esterase under the regulation of the same or a different promoter used to regulate the cephalosporin esterase coding sequence. Expression of the marker gene in response to induction or selection indicates the presence of the entire recombinant expression vector which carries the DNA sequence coding for all or part of cephalosporin esterase.

In the third approach, the production of cephalosporin esterase mRNA transcripts can be assessed by hybridization assays. For example, polyadenylated RNA can be isolated and analyzed by Northern blotting or nuclease protection assay using a probe complementary to the RNA sequence. Alternatively, the total nucleic acids of the host cell may be extracted and assayed for hybridization to such probes.

In the fourth approach, the expression of all or part of cephalosporin esterase can be assessed immunologically, for example, by Western blotting.

In the fifth approach, the expression of cephalosporin esterase protein can be assessed by complementation analysis. For example, in cells known to be deficient in this enzyme, expression of cephalosporin esterase activity can be detected on the enzymatic hydrolysis of a colorless substrate, p-nitrophenylacetate, to a yellow colored p-nitrophenylate on the media plate.

In the sixth approach, expression of cephalosporin esterase can be measured by assaying for cephalosporin esterase enzyme activity using known methods. For example, the assay described in the Examples section hereof may be employed.

The DNA sequences of expression vectors, plasmids or DNA molecules of the present invention may be determined by various methods known in the art. For example, the dideoxy chain termination method as described in Sanger et al., Proc. Natl. Acad. Sci. USA 74, 5463–5467 (1977), or the Maxam-Gilbert method as described in Proc. Natl. Acad. Sci. USA 74, 560–564 (1977) may be employed.

It should, of course, be understood that not all expression vectors and DNA regulatory sequences will function equally well to express the DNA sequences of the present invention. Neither will all host cells function equally well with the same expression system. However, one of ordinary skill in the art may make a selection among expression vectors, DNA regulatory sequences, and host cells using the guidance provided herein without undue experimentation and without departing from the scope of the present invention.

The present invention further concerns a method for producing cephalosporin esterase comprising culturing a host cell containing an expression vector capable of expressing cephalosporin esterase.

The present invention further concerns polypeptide molecules comprising all or part of cephalosporin esterase, said polypeptide molecules preferably having all or part of one of the amino acid sequence substantially as shown in FIG. 5. In the case of polypeptide molecules comprising part of cephalosporin esterase, it is preferred that polypeptide molecules be at least about 10 amino acids in length.

All amino acid residues identified herein are in the natural L-configuration. In keeping with standard polypeptide nomenclature, J. Biol. Chem. 243, 3557–3559 (1969), abbreviations for amino acid residues are as shown in the following Table of Correspondence:

TABLE OF CORRESPONDENCE

| SYMBOL | | |
|---|---|---|
| 1-Letter | 3-Letter | AMINO ACID |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

All amino acid sequences are represented herein by formulas whose left to right orientation is in the conventional direction of amino-terminus to carboxy-terminus.

The polypeptides of the present invention may be obtained by synthetic means, i.e., chemical synthesis of the polypeptide from its component amino acids, by methods known to those of ordinary skill in the art. For example, the solid phase procedure described in Houghton et al., Proc. Natl. Acad. Sci. 82, 5131–5135 (1985) may be employed. It is preferred that the polypeptides be obtained by production in prokaryotic or eukaryotic host cells expressing a DNA sequence coding for all or part of cephalosporin esterase, or by in vitro translation of the mRNA encoded by a DNA sequence coding for all or part of cephalosporin esterase. For example, the DNA sequence of FIG. 6 or 7 may be synthesized using PCR as described above and inserted into a suitable expression vector, which in turn may be used to transform a suitable host cell. The recombinant host cell may then be cultured to produce cephalosporin esterase. Techniques for the production of polypeptides by these means are known in the art, and are described herein.

The polypeptides produced in this manner may then be isolated and purified to some degree using various protein purification techniques. For example, chromatographic procedures such as ion exchange chromatography, gel filtration chromatography and immunoaffinity chromatography may be employed.

In addition to hydrolyzing 3' acetyl groups, the polypeptides of the present invention may be used in a wide variety of other ways. For example, the polypeptides may be used to prepare in a known manner polyclonal or monoclonal antibodies capable of binding the polypeptides. These antibodies may in turn be used for the detection of the polypeptides of the present invention in a sample, for example, a cell sample, using immunoassay techniques, for example, radioimmunoassay or enzyme immunoassay. The antibodies may also be used in affinity chromatography for purifying the polypeptides of the present invention and isolating them from various sources.

The polypeptides of the present invention have been defined by means of determined DNA and deduced amino acid sequencing. Due to the degeneracy nature of the genetic code, which results from there being more than one codon for most of the amino acid residues and stop signals, other DNA sequences which encode the same amino acid sequence as depicted in FIG. 5 may be used for the production of the polypeptides of the present invention. In addition, it will be understood that allelic variations of these DNA and amino acid sequences naturally exist, or may be intentionally introduced using methods known in the art. These variations may be demonstrated by one or more amino acid differences in the overall sequence, or by deletions, substitutions, insertions, inversions or additions of one or more amino acids in said sequence. Such amino acid substitutions may be made, for example, on the basis of similarity in polarity, charge, solubility, hydrophobicity, hydrophilicity and/or the amphiphatic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine, glycine, alanine, asparagine, glutamine, serine, threonine, phenylalanine, tyrosine. Other contemplated variations include salts and esters of the aforementioned polypeptides, as well as precursors of the aforementioned polypeptides, for example, precursors having N-terminal substituents such as methionine, N-formylmethionine used and leader sequences. All such variations are included within the scope of the present invention.

The following examples are further illustrative of the present invention. These examples are not intended to limit the scope of the present invention, and provide further understanding of the invention.

In the following examples, some reagents, plasmids, restriction enzymes and other materials were obtained from commercial sources and used according to the indication by suppliers. Operations employed for the purification and characterization and the cloning of DNA and the like are well known in the art or can be adapted from the literature.

EXAMPLE 1

Purification of Cephalosporin Esterase 1.1 Culture of Microorganism

*Rhodosporidium toruloides* (ATCC 10657) seed culture was initiated from the inoculation of frozen preservation cultures of 2% into 500 ml Erlenmeyer flasks containing 100 ml of the following medium: 2% glucose, 1% yeast extract, 1% Bacto-peptone, 0.5% $KH_2PO_4$, pH 6.0. Seed flasks were cultured for 24 hours at 28° C. and 250 rpm; 2% inoculum volume was used to start production stage fermentations. Production stage medium was composed of: 8% corn steep liquor, 1% $KH_2PO_4$, 3% glucose, pH 6.2. The media was autoclaved for two hours. This led to increased titers when compared to the normal autoclave time of 30 minutes. Fermentor broth was cultured for 3 or 4 days to 16°–21° C. with high aeration. Specific activities of whole broth were typically in the range of 20–37 IU/mi.

1.2 Purification of the Enzyme From *Rhodosporidium Toruloides*

The esterase was released from *Rhodosporidium toruloides* cells by treatment of the fermentation broth with 100 mM EDTA at pH 4.0 for 8 hours. Approximately 50% of the enzymatic activity could be released from the cells in this manner. The broth was centrifuged at 5000 g to remove the cells and the corn steep solids. The supernatant was ultra-filtered through an Amicon hollow fiber cartridge with a molecular weight cut-off of 30,000 to 10% of the original volume. The enzyme was brought up to the original volume by addition of deionized water. The pH was brought up to 7.0 by addition of 2M ammonium hydroxide and the enzyme solution added to DEAE Trisacryl (100 g resin/50 ml enzyme solution) which had been washed with 50 mM potassium phosphate buffer 7.0. The enzyme does not bind to DEAE and was obtained in the filtrate which was then brought to pH 4.5 with 1.0M acetic acid. This solution was then loaded onto a carboxymethyl Sepharose column (18×3 cm) and washed with 50 mM ammonium acetate pH 4.5 until the absorbance at 280 nm was less than 0.1 (approximately 4 column volumes). The esterase was eluted with a linear gradient of 50 to 500 mM ammonium acetate pH 6.5 (flow rate 1.0 ml/min). Fractions of 7.0 ml were collected and the fractions containing esterase were pooled and concentrated on a 50,000 molecular weight cut off Centricon.

EXAMPLE 2

Characterization of Cephalosporin Esterase 2.1 Specific Activity of Enzyme

Enzyme was added to the reaction mixture containing the potassium salt of the cephalosporin (25–400 mM), 100 mM potassium phosphate, pH 6.5 in a final volume of 0.5 ml. The mixture was incubated at 30° C. (unless described otherwise) and stopped by addition of 2.0 ml 50% acetonitrile. The reaction was monitored at 254 nm by HPLC on a 5 micron C18 column (50×4 mm) with the mobile phase consisting of 25 mM octane sulfonic acid, 0.1% phosphoric acid, 12% methanol, pH 2.5. Protein was assayed using the Bio-Rad protein assay kit (Bio-Rad Co., USA) using bovine serum albumin as the standard. The enzyme exhibited Michaelis-Menton kinetics with cephalosporin C. From double reciprocal plots, the $K_m$ for hydrolysis of cephalosporin C was found to be 51.8 mM with a corresponding $V_{max}$ of 77.0 μmole/min/mg. The reaction products, desacetyl cephalosporin C and acetate did not inhibit the reaction to any appreciable extent. A 1.0% solution of cephalosporin C was completely hydrolyzed within 30 minutes at 30° C. with no side products observed by HPLC.

2.2 Substrate File

Esterase activity was measured using p-nitrophenyl ester substrates as well as cephalosporin derivatives. The enzyme was incubated at 30° C. (unless described otherwise) with p-nitrophenyl acetate, 10.0 mM in 100 mM potassium phosphate buffer pH 6.5 or 10.0 mM p-nitrophenyl esters ranging in carbon chain length from C:2 to C:18 in 100 mM potassium phosphate pH 6.5 and 2% acetonitrile. Enzyme activity was monitored spectrophotometrically by measuring the increase in absorbance at 405 nm due to the formation of the p-nitrophenylate ion. The assay for cephalosporin derivatives was as described in Example 2.1. The results are described in Table 1 for p-nitrophenyl ester substrates and Table 2 for cephalosporin derivatives.

TABLE 1

Effect of Increasing Ester Chain Length on Esterase Activity.

| Length of Ester | Relative Activity (%) |
|---|---|
| Acetate C:2 | 100 |
| Propionate C:3 | 34 |
| Butyrate C:4 | 5 |
| Caproate C:6 | 0 |
| Caprylate C:8 | 0 |
| Caprate C:10 | 0 |
| Laurate C:12 | 0 |
| Myristate C:14 | 0 |
| Palmitate C:16 | 0 |
| Stearate C:18 | 0 |

TABLE 2

Relative rates of esterase acitivity against cephem substrates

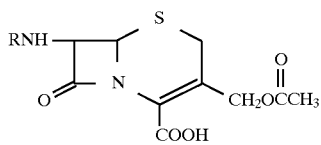

| Substrate | Relative Rate |
|---|---|
| R = —H | 100 |
| —C(O)CH$_3$ | 51 |
| —C(O)CH$_2$Cl | 105 |
| —C(O)CHCl$_2$ | 108 |

TABLE 2-continued

Relative rates of esterase acitivity against cephem substrates

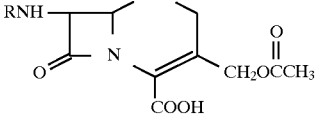

| Substrate | Relative Rate |
|---|---|
|  —CCH₂Br | 114 |
| 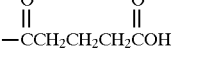 —CCH₂I | 103 |
| —CCH₂CH₂CH₂COH (with two C=O) | 105 |
| —CCH₂CH₂CH₂CHCOH, NH₂ (with two C=O) | 68 |
| —CCH₂CH₂CH₂CHCOH, NHCCH₃ with C=O (with two C=O) | 42 |
| 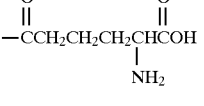 —CCH₂—(phenyl) | 17 |
| 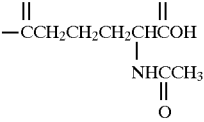 —CCH₂—(phenyl)—CH₃ | 68 |
| 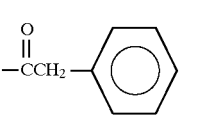 —CCH₂—(phenyl)—OCH₃ | 41 |
| 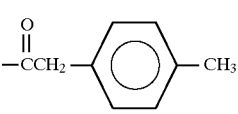 —CCH₂—(thiophene) | 34 |

TABLE 3

| Effector | Relative Activity (%) |
|---|---|
| None | 100 |
| β-Mercaptoethanol | 137 |
| Dithiothreitol | 115 |
| Iodoacetamide | 104 |
| N-ethylmaleimide | 85 |
| Phenylmethylsulfonyl fluoride | 53 |
| 3,4-Dichloroisocoumarin | 43 |
| Dimethyl phosphite | 51 |
| Diethyl pyrocarbonate | 7 |
| MgCl₂ | 100 |
| MnCl₂ | 97 |
| ZnCl₂ | 93 |

TABLE 3-continued

| Effector | Relative Activity (%) |
|---|---|
| CaCl₂ | 95 |
| EDTA | 82 |

2.3 Effect of Temperature

A. Optimum Temperature

Enzyme was incubated with p-nitrophenyl acetate, 10.0 mM n 100 mM potassium phosphate buffer pH 6.5. The reaction mixtures were incubated for 10 minutes in a shaking water bath at 300 rpm at temperatures from 10° to 65° C. The optimal temperature for the reaction was 25° C. The results are shown in FIG. 1.

B. Thermal Stability

Figure 2:
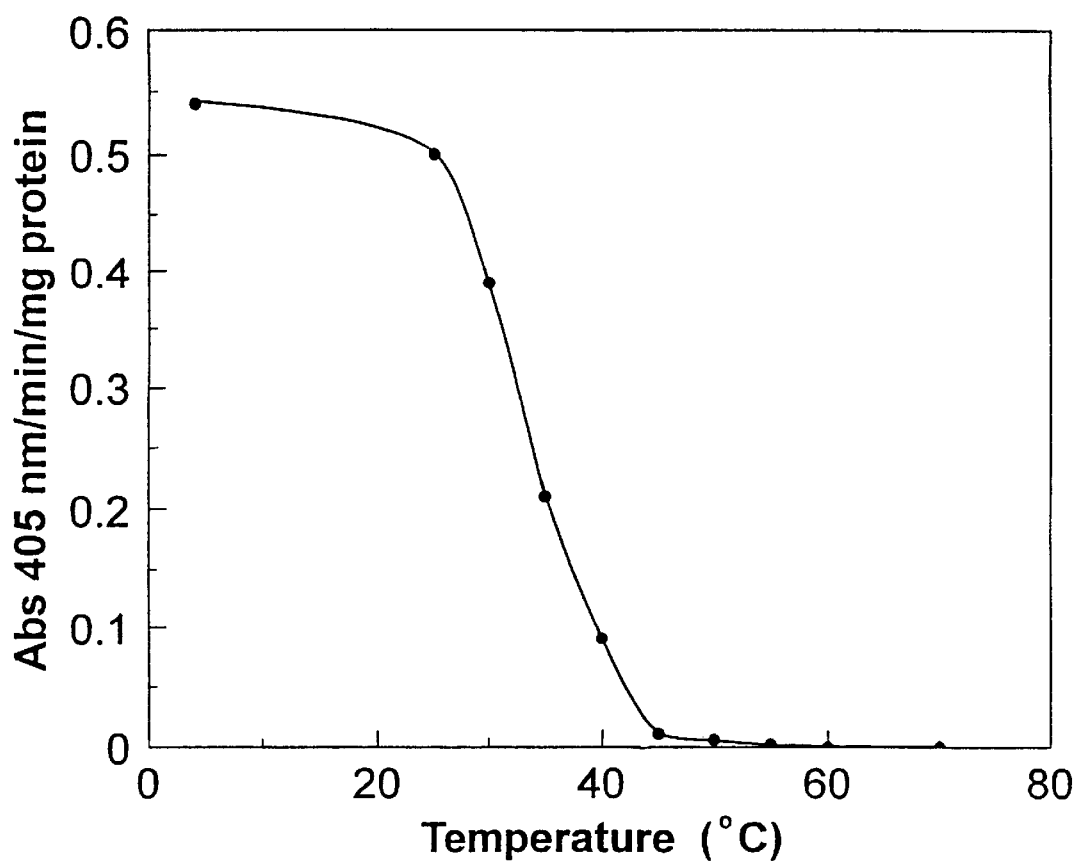
FIG. 2 The thermal stability of the cephalosporin esterase.

Enzyme was incubated with p-nitrophenyl acetate as described in Example 2.3A. Enzyme was incubated at various temperatures for 15 minutes then immediately placed on ice. The enzyme was unstable when incubated at temperatures about 25° C. with rapid inactivation between 30° and 45° C. The results are shown in FIG. 2.

2.4 Effect of pH

Figure 3:
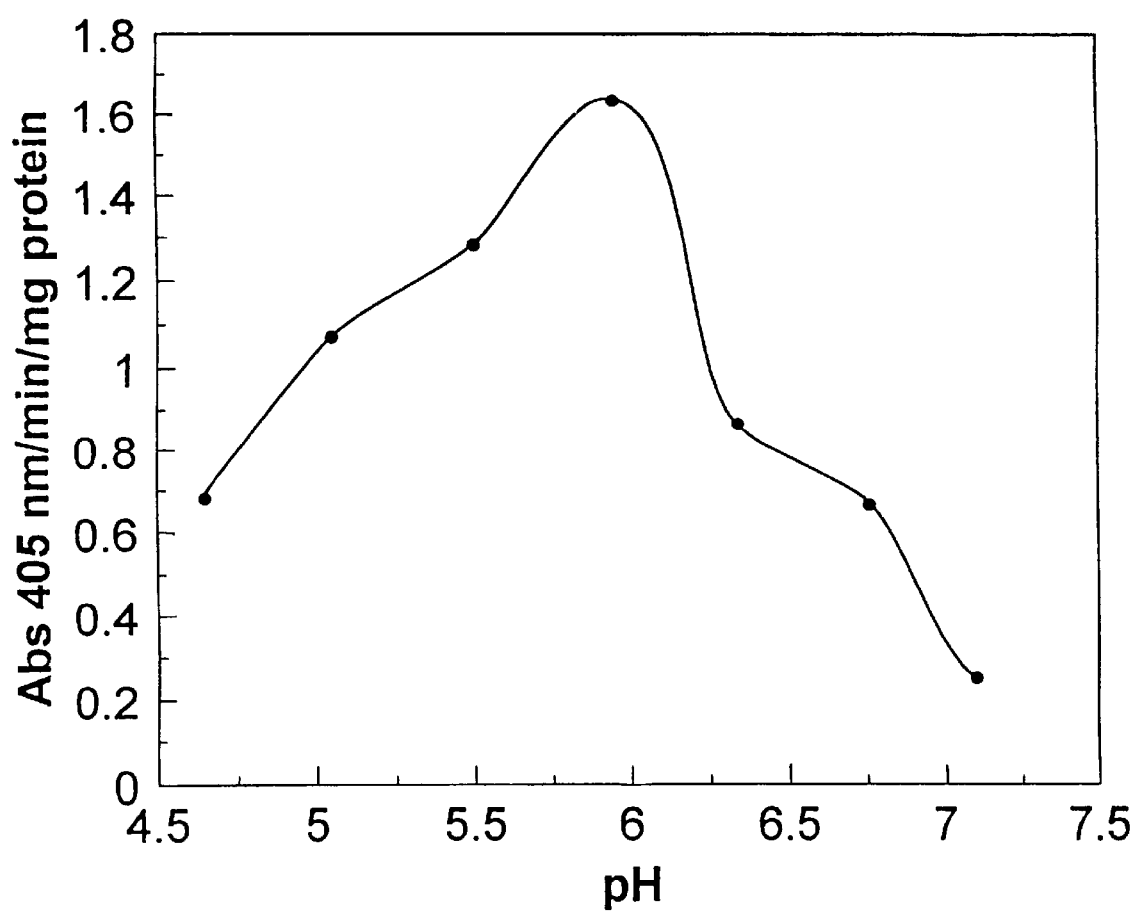
FIG. 3 The pH optimum of the cephalosporin esterase.

Enzyme was incubated with p-nitrophenyl acetate as described in Example 2.3A. A 100 mM Tris-maleate universal buffer with a pH range of 4 to 8 was used. The esterase was found to be active in a pH range of 4.5 to 7 with optimal activity at a pH of 6.0 with both p-nitrophenyl acetate and cephalosporin C. The results with p-nitrophenyl acetate are shown in FIG. 3.

2.5 Effect of Various Enzyme Modulators

Enzyme was incubated in the presence of 10 mM reagent for 15 minutes at 25° C. The reaction mixture was then diluted 100 fold into assay mix and assayed with p-nitrophenyl acetate. The results are summarized in Table 3. The results strongly suggests the presence of an active-site serine for the Rhodosporidium enzyme. Phenylmethylsulfonyl fluoride (PMSF), 3,4-dichloroisocoumarin (DCI), and dimethyl phosphite all inhibited the enzyme. The histidine-modifying reagent diethylpyrocarbonate essentially inactivated the enzyme. Sulfhydryl-modifying agents iodoacetamide and N-ethylmaleimide had little or no effect on the activity of the enzyme although slight activation was observed with β-mercaptoethanol and dithiothreitol. The presence or absence of metal ions also had little or no effect on the enzyme although slight inhibition was observed with EDTA.

2.6 Determination of Isoelectric Point (pI).

Isoelectric focusing gels were run using the Ampholine PAGplate system developed by Pharmacia Biotech (Sweden) in the pH range of 3–9. pI was also determined using the MinpHor system developed by Rainin Co. (USA) with the broad range ampholyte mixture pH 3–9. The isoelectric point of the protein was determined to be approximately 5.6.

2.7 Determination of Molecular Weight

Molecular weight was determined by gel permeation chromatography and gel electrophoresis. SDS-PAGE gels (gradient 8–25%) were run according to the method of Laemmli (Laemmli, U.K. 1970. Cleavage of structural proteins during the assembly of the head of bacteriophage T4. Nature (London) 227:680–685). Proteins were stained with Coomassie brilliant blue. Gel permeation chromatography was performed by HPLC on a 75×300 mm TosoHaas TSK-GEL GS3000SW XL column with a mobile phase of 200 mM potassium phosphate pH 6.8, 150 mM sodium chloride. Bio-Rad gel filtration standard mixture (MW 670,000-1,350) was used as the marker. The flow rate was 1.0 ml/min and the eluate was monitored at 280 nm. Fractions were collected and assayed for esterase activity. A single band at 80,000 Da was observed by SDS-PAGE; gel filtration chromatography of the enzyme indicated that the enzyme is a monomer in the native state.

2.8 Determination of Carbohydrate Content of Enzyme

Removal of carbohydrate with recombinant peptide N-glycosidase was performed as described by Elder et al. and endoglycosidase H as performed by Trimble et al. Native and deglycosylated enzyme were then analyzed by SDS-PAGE as described in Example 2.7 to determine carbohydrate loss. Treatment of the enzyme with endoglycosidases resulted in a 15–20% reduction of molecular weight to approximately 62,000 Daltons.

2.9 Determination of N-Terminal Amino Acid Sequence

The amino-terminal sequence was determined by automated Edman degradation at the Cornell University Biotechnology Analytical Facility. The amino terminal sequence is shown in FIG. 4.

3.0 Preparation of Chromosomal DNA of R. toruloides

Seed media culture was inoculated at 4% with a frozen culture of Rhodosporidium toruloides (ATCC 10657). The culture was grown at 28° C. for 24 hours in 2% glucose, 1% yeast extract, 1% bacto-peptone, 0.5% $KH_2PO_4$, pH 6.0. Cells were harvested by centrifugation and washed once in buffer containing: 1M sorbitol, 50 mM sodium citrate pH 5.4. Cells were centrifuged again and resuspended in wash buffer containing 0.5% lysing enzymes (Sigma Chemical Co., USA) at 37° C. for 3 hours. Spheroplasts were collected by centrifugation and digested in 100 mM NaCl, 10 mM Tris-HCl pH 8.0, 25 mM EDTA, 01% SDS and 100 μg/ml proteinase K. The solution was incubated at 50° C. for 16 hours. The mixture was extracted twice, first with phenol:chloroform:isoamyl alcohol (24:24:1), then with chloroform:isoamylalcohol (24:1) and the DNA was precipitated with ethanol (70%). The DNA was recovered by centrifugation and washed with 70% ethanol. The DNA pellet was dissolved in TE (10 mM Tris-HCl pH 8.0, 1mM EDTA) and 100 μg/ml Rnase A and incubated for at 37° C. for 16 hours. The organic extractions and ethanol precipitations were repeated and the DNA was dissolved in TE. The DNA concentration was determined spectrophotometrically.

3.1 Construction of Genomic DNA Library of R. Toruloides

From the N-terminal amino acid sequence (section 2.9) four 17-omer oligonucleotide probes were synthesized (FIG. 4), end-labeled with [γ-32P]ATP, and used to probe a southern blot of R. toruloides chromsomal DNA digested with restriction endonucleases BamH1 and Pst1. Hybridization was conducted in TMAC (tetramethylammoniumchloride, Sigma chemical Co.) buffer at 46.8° C. for 48 hours. A 3 kb BamH1 fragment hybridized to one of the probes. The 3 kb BamH1 fragment was isolated and ligated to pBluescript KS+ phagemid (Stratagene, USA) cleaved with BamH1 and treated with bacterial alkaline phosphatase. The ligation mixture was used to transform E. coli XL1-blue cells by electroporation at 2.5 kvolts, 200 ohms, 25 μFd. The transformants were selected onLB agar containing 100 μg/ml ampicillin.

3.2 Selection of Clone Containing Cephalosporin Esterase Gene

Colony blots of the genomic library were prepared and screened with the N-terminal oligonucleotide probe. Twelve clones were initially selected for further evaluation. Plasmid DNA was isolated from each transformant using the TELT mini-prep method (He et al. 1990 Nucl. Acid Res., 18:1660). Southern analysis of these clones identified two that hybridized to the probe. Translation of the adjacent DNA sequence produced an amino acid sequence that was identical to the N-terminal protein sequence. Further analysis of the 3 kb BamH1 fragment by primer extension and southern blotting determined the location and orientation of the esterase gene within the fragment.

3.3 cDNA Cloning

A cDNA clone was produced by 3'RACE (rapid amplification of cDNA ends, BRL Co., USA). Total RNA from R. toruloides was isolated using Trizol reagent (BRL Co., USA) and further purified by lithium chloride precipitation. First strand cDNA was prepared by reverse transcription from an adapter primer. The RNA template was digested with Rnase H and the cDNA was amplified by PCR using a gene-specific primer and an adapter primer. The coding region was amplified and mutagenized by a second round of PCR using an internal gene-specific primer which included the putative translation start site and an Nco1 restriction site at the translation start site for subsequent cloning into expression vectors. This produced a 1.9 kb fragment which was gel purified. Restriction analysis and nucleotide sequencing of this fragment confirmed that it contained the esterase gene. To further facilitate cloning into an expression vector, another cDNA clone was developed that included a BspH1 site at the beginning of the mature peptide and a BamH1 site at the 3-end of the gene.

3.4 Determination of Nucleotide Sequence

The nucleotide sequence was determined by the dideoxy chain termination method (Sanger et al., 1977 Proc. Natl. Acad. Sci. USA 74:5463–5467) using the Taq Track fmol DNA sequencing systems (Promega Co., USA). T3, T7, and synthesized internal primers were used to sequence the entire gene from both strands. Electrophoresis was performed on a 7% Long Ranger (AT Biochem. Co., USA) polyacrylamide gel containing 7M urea in TBE buffer at 2700 volts. The complete nucleotide sequence is shown in FIG. 5. The coding cDNA region is 1716 bp long and codes for a 572 amino acid protein of molecular weight 61.3 kD. This is consistent with the deglycosylate form of the enzyme (Section 2.8). The N-terminal protein sequence determined from the DNA sequence is identical to the protein sequence identified in section 2.9. This sequence begins 28 residues down from the putative ATG translation start site. The cDNA clone was also sequenced for comparison to the genomic clone. The gene contains five introns which are identified in FIG. 7.

What is claimed is:

1. An isolated DNA molecule having the nucleotide sequence of SEQ. ID. NO.:1.

2. An isolated DNA molecule having the nucleotide sequence of SEQ. ID. NO.:3.

3. An isolated DNA molecule having the nucleotide sequence of SEQ. ID. NO.: 5.

4. An isolated DNA molecule having the nucleotide sequence of SEQ. ID. NO.: 6.

5. An isolated DNA molecule having the nucleotide sequence of SEQ. ID. NO.: 7.

6. An isolated DNA molecule having the nucleotide sequence of SEQ. ID. NO.:8.

7. An isolated nucleic acid molecule having a sequence coding for the amino acid sequence of SEQ. ID. NOS: 2 or 4.

8. An isolated nucleic acid molecule having a sequence complementary to a nucleic acid sequence coding for the amino acid sequence of SEQ. ID. NOS: 2 or 4.

9. The nucleic acid molecule of claim 7 which is a DNA molecule.

10. The nucleic acid molecule of claim 8 which is a DNA molecule.

11. An expression vector comprising:
    (a) a nucleic acid molecule having a sequence coding for the amino acid sequence of SEQ ID NOs: 2 or 4; or
    (b) a nucleic acid molecule having a sequence complementary to (a).

12. The expression vector of claim 11 further comprising an origin of replication, a promoter, and a transcription termination sequence.

13. The expression vector of claim 12 further comprising a selectable marker sequence.

14. The expression vector of claim 12 which is capable of integrating into fungal chromosomes.

15. The expression vector of claim 11 which is a plasmid.

16. The expression vector of claim 11 having the DNA sequence of SEQ. ID. NOS.:1 or 3.

17. A host cell containing the expression vector of claim 11.

18. A host cell containing the expression vector of claim 14.

19. A host cell containing the expression vector of claim 16.

20. The host cell of claim 17 which is eukaryotic.

21. The host cell of claim 18 which is eukaryotic.

22. The host cell of claim 17 selected from the group consisting of the species *Escherichia coli, Rhodosporidium toruloides, Cephalosporium acremonium*, and *Penicillium chrysogenum*.

23. The host cell of claim 17 which is the species *Cephalosporium acremonium*.

24. A method for producing a polypeptide having cephalosporin esterase activity, said method comprising the steps of:
    culturing the host cell of claim 17 under conditions resulting in expression of the polypeptide; and
    isolating the expressed polypeptide.

* * * * *